United States Patent
Le et al.

(10) Patent No.: US 9,423,407 B2
(45) Date of Patent: Aug. 23, 2016

(54) AUTOMATED ANALYSIS COVERAGE VERIFICATION (AACV)

(71) Applicant: WESTINGHOUSE ELECTRIC COMPANY LLC, Cranberry Township, PA (US)

(72) Inventors: Qui V. Le, Pittsburgh, PA (US); Craig Bowser, North Huntingdon, PA (US); Stephen Beehner, Greensburg, PA (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 601 days.

(21) Appl. No.: 13/628,255

(22) Filed: Sep. 27, 2012

(65) Prior Publication Data

US 2013/0085684 A1    Apr. 4, 2013

Related U.S. Application Data

(60) Provisional application No. 61/541,313, filed on Sep. 30, 2011.

(51) Int. Cl.
| | |
|---|---|
| *G01N 35/00* | (2006.01) |
| *G06F 17/00* | (2006.01) |
| *F22B 35/00* | (2006.01) |
| *F22B 37/00* | (2006.01) |
| *F22B 35/18* | (2006.01) |

(52) U.S. Cl.
CPC .............. *G01N 35/00* (2013.01); *F22B 35/004* (2013.01); *F22B 35/18* (2013.01); *F22B 37/003* (2013.01); *G06F 17/00* (2013.01)

(58) Field of Classification Search
CPC ................ G01N 1/00; G01N 27/9046; G01N 2223/419; G01N 223/628; G06Q 10/00; F22B 1/00; F22B 37/002; Y02E 30/40; G05B 23/0254
USPC .............. 324/220, 238, 229; 702/38, 34, 179, 702/127, 35
See application file for complete search history.

(56) References Cited

U.S. PATENT DOCUMENTS

| | | | | |
|---|---|---|---|---|
| 4,235,020 A | * | 11/1980 | Davis ...................... | G01B 7/13 324/220 |
| 4,253,768 A | | 3/1981 | Yaroshuk et al. | |
| 4,341,113 A | * | 7/1982 | Gutzwiller, Jr. ....... | G01B 7/287 324/220 |

(Continued)

OTHER PUBLICATIONS

International Preliminary Report on Patentability for PCT/US2012/057720 dated Apr. 1, 2014 (Forms PCT/IB/373, PCT/ISA/237).

(Continued)

*Primary Examiner* — Toan Le
*Assistant Examiner* — Jeffrey Aiello
(74) *Attorney, Agent, or Firm* — Richard J. Coldren; Westinghouse Electric Company LLC

(57) ABSTRACT

The invention relates to systems and methods for verifying complete analysis coverage in a steam generator tube inspection. The analysis is conducted by an automated analysis process. The process includes setup and analysis functions. Information is entered into the setup function to identify abnormalities to be inspected and to model the steam generator tubes. The verification includes employing a software verification program to detect and identify a gap within analysis coverage for a particular abnormality or set of abnormalities for which the steam generator tube is inspected, in a particular portion of the steam generator tube.

16 Claims, 2 Drawing Sheets

(56) References Cited

U.S. PATENT DOCUMENTS

| | | | |
|---|---|---|---|
| 4,567,774 | A | 2/1986 | Manahan et al. |
| 4,724,298 | A | 2/1988 | Hawkins et al. |
| 4,763,274 | A * | 8/1988 | Junker et al. .................... 702/38 |
| 4,891,767 | A * | 1/1990 | Rzasa .................... B25J 9/1697 |
| | | | 382/151 |
| 7,885,381 | B2 * | 2/2011 | Nagumo et al. ................ 378/59 |
| 8,000,936 | B2 | 8/2011 | Davis |
| 2003/0065454 | A1 * | 4/2003 | Perdue et al. .................... 702/34 |
| 2003/0195710 | A1 * | 10/2003 | Junker et al. .................... 702/65 |
| 2005/0154564 | A1 * | 7/2005 | Le .................... G01N 27/902 |
| | | | 702/189 |
| 2008/0071501 | A1 * | 3/2008 | Herzog .................... F22B 37/10 |
| | | | 702/185 |
| 2009/0063113 | A1 | 3/2009 | Francino et al. |
| 2009/0292574 | A1 * | 11/2009 | Pop et al. .................... 705/8 |
| 2011/0022333 | A1 * | 1/2011 | Griffith et al. .................... 702/46 |
| 2011/0172964 | A1 * | 7/2011 | Le .................... 702/183 |
| 2011/0172980 | A1 * | 7/2011 | Le .................... 703/7 |
| 2012/0065927 | A1 * | 3/2012 | Le et al. .................... 702/150 |
| 2012/0081108 | A1 * | 4/2012 | Le .................... G01N 27/9046 |
| | | | 324/220 |
| 2012/0257705 | A1 * | 10/2012 | Le .................... 376/249 |
| 2013/0335551 | A1 * | 12/2013 | Mandier et al. ................ 348/84 |

OTHER PUBLICATIONS

Nadinic et al, Eddyone Automated Analysis of PWR/WWER Steam Generator Tubes Eddy Current Data. 5th Intn'l Conf. on Nuclear Option in Countries with Small and Medium Electricity Grids, Dubrovnik, Croatia, May 20, 2004, pp. 1-11. [retrieved on Nov. 24, 2012] Retrieved from the internet <https://bib.irb.hr/datoteka/178372.s-3_14.pdf> entire doc.

Supplementary European Search Report dated Apr. 21, 2015 for EP12835422.

* cited by examiner

ROI VISUAL VIEW

COLUMN 1

10 DENTS
11 DINGS
12 TS FLAWS

COLUMN 2
40 41 42
20
21
22
23
24
25
26
27
28
29
30

COLUMN 3
20L
21L
22L
23L
24L — 60
25L
26L
27L
28L
29L
30L

Gap Analysis Summary

⊗ 1 GAP detected
Gap detected near 24L
Please see gap detail on ROI Visual View

*FIG. 3*

AUTOMATED ANALYSIS COVERAGE VERIFICATION (AACV)

CROSS REFERENCE TO RELATED APPLICATION

This application claims priority to Provisional Application Ser. No. 61/541,313, filed Sep. 30, 2011, entitled AUTOMATED ANALYSIS COVERAGE VERIFICATION (AACV).

BACKGROUND

1. Field

This invention pertains to software tools and methods to verify analysis coverage for steam generator tube inspection. In particular, the software tools and methods of the invention verify analysis coverage for the following two automated analysis processes: Enhanced Automated Data Screening (EADS) and Real Time Automated Analysis (RTAA).

2. Description of Related Art

Steam generator tube inspection is known in the art. Further, it is known that there are disadvantages associated with automated analysis processes known in the art for use in steam generator tube inspections. For example, there may be incomplete coverage or a gap in the automated analysis setup which can lead to an area of the steam generator tube not being analyzed or being analyzed improperly. Such a lack of coverage or gap may cause steam generator tube degradation to be undetected. Undetected degradation can progress and result in various problems and failures. For instance, undetected degradation in a steam generator installed in a nuclear power plant could result in an unscheduled outage.

EADS and RTAA are two automated analysis processes known in the art for use in inspecting steam generator tubes for degradation. It is desired to design and develop verification tools and methods that are capable to provide at least one of the following advantages: detection of unanalyzed area or gap in analysis coverage, identification of the location of the unanalyzed area or gap relative to the steam generator tube, and assessment of the acceptability of the unanalyzed area or gap. As a result of performing coverage verification, it may be demonstrated that there is complete tube analysis coverage, or that there is incomplete tube coverage but the unanalyzed areas or gaps are acceptable, or there is incomplete tube coverage and the unanalyzed areas or gaps are unacceptable and therefore, need to be addressed.

SUMMARY

In one aspect, this invention provides a computer software system for verifying complete analysis coverage in a steam generator tube inspection. The system includes an automated analysis process having setup and analysis functions. The setup includes an auto analysis sort of abnormalities for which a steam generator tube is inspected and a mapping of the steam generator tube into a plurality of segments. Each segment has associated therewith a length of the steam generator tube. The system further includes a software verification program to detect and identify a gap within analysis coverage for a particular abnormality or set of abnormalities for which the steam generator tube is inspected.

In another aspect, this invention provides a computer method for verifying complete analysis coverage in a steam generator tube inspection. The method includes employing an automated analysis process having setup and analysis functions. The setup includes entering information comprising selecting an auto analysis sort of one or more abnormalities for which a steam generator tube is being inspected and mapping the steam generator tube into a plurality of segments. Each segment has associated therewith a length of the steam generator tube. The method further includes employing a software verification program for detecting and identifying a gap within analysis coverage for a particular abnormality within the one or more abnormalities for which the steam generator tube is inspected, and for one or more segments of the plurality of segments.

BRIEF DESCRIPTION OF THE DRAWINGS

A further understanding of the invention can be gained from the following description of the preferred embodiments when read in conjunction with the accompanying drawings in which:

FIG. 3 shows the gap analysis of FIG. 2 and notification of a gap in analysis coverage in accordance with certain embodiments of the invention.

DESCRIPTION OF THE PREFERRED EMBODIMENT

The invention relates to software tools and methods to verify complete analysis coverage of areas of interest for steam generator tube inspection. These software tools and methods are applicable to various steam generator designs and the processes employed for inspection of the tubes disposed therein. In certain embodiments of the invention, the steam generator is positioned within a nuclear reactor plant, such as a pressurized water reactor plant or a boiling water reactor plant. Steam generator tube inspections typically employ an automated analysis process which includes setup and, subsequently, analysis. If the setup, e.g., configuration parameters, does not provide for complete coverage of all areas of interest for steam generator tube inspection, there is a potential for a lack of coverage or a gap in coverage of one or more areas of interest.

The invention provides verification tools and methods to reduce, minimize or preclude incomplete coverage or gaps in the analysis of all areas of interest analyzed in the steam generator tube inspection. These verification tools and methods can identify an unanalyzed area or a gap, provide notification of the unanalyzed area or gap, identify the location of the unanalyzed area or gap along the length of the steam generator tube, and provide for assessment to be made as to whether the unanalyzed area or gap is acceptable or unacceptable. If acceptable, no further action may be needed. If unacceptable, further action may be taken to address and resolve the unanalyzed area or gap.

There are various automated analysis processes known in the art for use in performing steam generator tube inspections to determine and assess degradation. Non-limiting examples of automated analysis processes include known software programs, such as Enhanced Automated Data Screening (EADS) and Real Time Automate Analysis (RTAA). Various known computer systems can be employed to run and operate these software programs.

Figure 1:
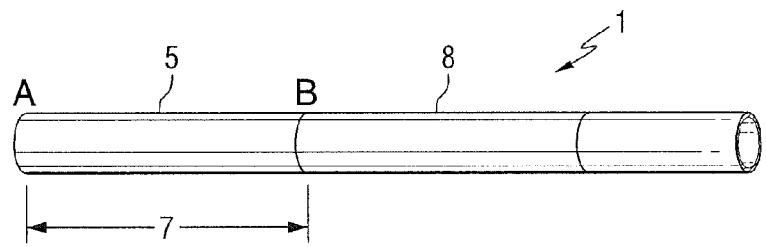
FIG. 1 shows a schematic of a steam generator tube segment in accordance with certain embodiments of the invention.

The setup for each of the EADS and RTAA processes generally includes mapping the steam generator tubes to be inspected and the supporting structures. The configuration parameters for the tubes and structures are input into a setup portion of the software program. For example, the information entered into the setup can include the number of steam generator tubes, the length of the steam generator tubes, and the like. This information can be specific to particular steam generator designs and nuclear reactor plants. In certain embodiments, steam generator tubes can be mapped as follows. The length of each of the steam generator tubes is partitioned into a plurality of segments. The length of each segment is measured and recorded. In this embodiment, a landmark is established and the offset from the landmark is measured. The landmark represents one endpoint of the segment and the offset represents the distance or length to the other endpoint of the segment. This is illustrated in FIG. 1. FIG. 1 shows a steam generator tube 1 in accordance with certain embodiments of the invention. A segment 5 of the steam generator tube 1 extends from a point A to a point B. The point A is the landmark and the point B is the end point of the segment 5. A distance or length 7 from the point A to the point B is the offset. This segmentation process can be carried out until a specified steam generator tube distance is covered. In certain embodiments, this process is carried out initiating with the steam generator tube end at the hot leg, extending through the u-bend and ending with the tube end at the cold leg. Thus, the landmark is located at the tube end of the hot leg and the offset therefrom is determined for each successive end point or segment. Alternatively, an end point for one segment can then serve as the landmark for another (consecutive) segment. This is illustrated in FIG. 1. FIG. 1 shows a segment 8 of the steam generator tube 1. The segment 8 is disposed adjacent to the segment 5. The point B is both the end point of the segment 5 and the landmark of the segment 8.

The setup for the automated analysis process further includes the potential to selectively analyze the steam generator tubes for various abnormalities and degradation. This is referred to as the auto analysis sort. The mode of analysis can vary and include degradation detection, tube geometry variation and/or loose part detection. In certain embodiments, the auto analysis sort can include dents, dings, flaws and the like. The analysis process provides the capability to selectively inspect the steam generator tubes for only one abnormality or, alternatively, to inspect for a plurality of abnormalities. For example, each of the segments 5 and 8 of steam generator tube 1 in FIG. 1, described above, can be analyzed for a particular abnormality or a plurality of abnormalities, such as but not limited to dents, dings, and flaws.

The analysis coverage verification for EADS includes the following two parts: a Gap Analysis Tool (GAT) and an Automated Report Extent Verification. The GAT provides a visual display of EADS coverage for a given steam generator model. Therefore, a visual verification of complete coverage and the absence or presence of gaps in coverage can be observed for each mode of the analysis. Thus, for example, GAT can show coverage for analysis of dents, dings and flaws for each segment of a steam generator tube. Further, GAT can show if a particular segment of the steam generator tube was not analyzed for one or more of dents, dings and flaws. EADS creates an automated report that contains the extent of the analysis and includes error messages to identify any analysis mode coverage problems, e.g., gaps in analysis. For example, the automated report can generate an error message to identify the particular segment of a steam generator tube that was not analyzed for one or more of dents, dings and flaws. The report is loaded into a database and analysis extent verification is performed to confirm that the extent of the analysis meets the inspection planned extent.

RTAA performs additional verification in real time for each steam generator tube analyzed. The RTAA checks for each data point within the planned inspection extent to ensure that it has been measured by at least one method of noise measurement, such as free span noise measurement or a structure-related noise measurement. If there is a gap in noise measurements, which may be indicative of a gap in coverage, RTAA will abort and create an error message in the noise monitoring log. The noise measurement values are loaded into a database and a final check of all expected noise measurements is conducted. The database provides verification for each region of interest (ROI) that the number of noise measurements is within the expected tolerance and that the value of the noise measurements is also as expected. Extreme deviation from the number of measurements or the expected value of measurements will be flagged for disposition.

The software tools and methods of the invention verify that each of the segments identified and/or modeled in the setup for EADS and RTAA are analyzed. The mode of analysis can vary and, as above-identified, can analyze for a wide variety of conditions. For example, the mode of analysis can include an analysis of steam generator tube abnormalities, such as dents, dings, flaws and the like. Further, the software tools and methods of the invention can detect if there is a lack of analysis or a gap in analysis for EADS and RTAA. Furthermore, the tools and methods identify the particular segment or location of the steam generator tube where the lack of analysis or gap occurs. Once the unanalyzed area is detected and identified, it can be analyzed to determine whether or not the gap is acceptable, e.g., there is an explanation for the gap, or if the gap is unacceptable, e.g., unexplainable and, therefore, needs to be addressed.

Figure 2:
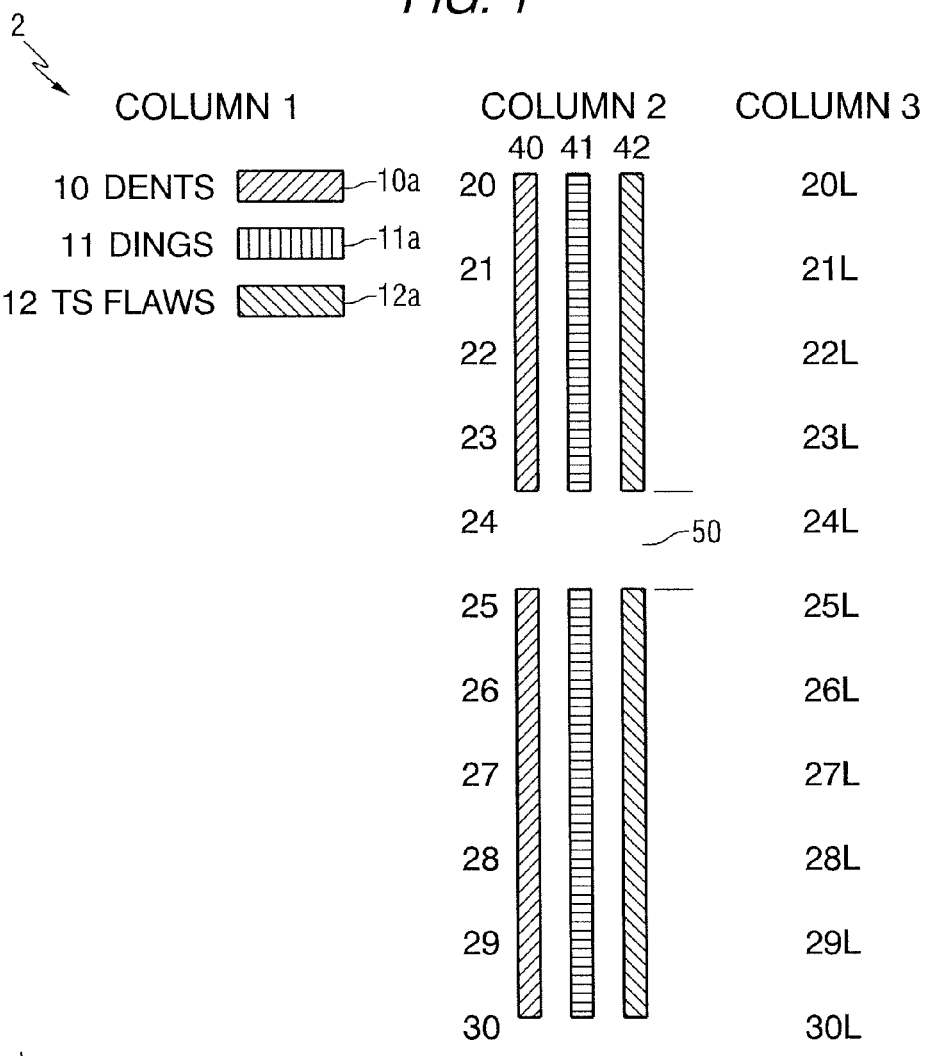
FIG. 2 shows a gap analysis including an auto analysis sort and steam generator tube model in accordance with certain embodiments of the invention.

FIG. 2 shows a gap analysis 2 in accordance with certain embodiments of the invention. FIG. 2 includes setup and verification portions of an automated analysis process described herein for use in performing a steam generator tube inspection. Column 1 identifies the auto analysis sort which includes the modes for which the steam generator tubes are being analyzed. As shown in Column 1, the steam generator tubes are being analyzed for dents 10, dings 11, and tube sheet flaws 12. Each of the dents 10, dings 11, and tube sheet flaws 12 correspond to or are represented by a different shading 10a, 11a and 12a, respectively. In certain embodiments, each of the dents 10, dings 11, and tube sheet flaws 12 can correspond to a different color. For example, dents 10, dings 11, and tube sheet flaws 12 can each correspond to red, blue and yellow, respectively.

Further, FIG. 2 shows points 20 through 30 vertically spaced and positioned in Column 2. The points 20 through 30 represent end points used to model segments of a steam generator tube. Furthermore, points 40 through 42 are horizontally spaced and positioned in Column 2 and correspond to the vertical shaded bars extending downward therefrom. The point 20 corresponds to the steam generator tube end at the hot leg (e.g. of the reactor coolant system (RCS) in a nuclear reactor plant) and the point 21 corresponds to the tube sheet of the steam generator at the hot leg. The point 29 corresponds to the steam generator tube sheet at the cold leg (e.g. of the RCS) and the point 30 corresponds to the steam generator tube end at the cold leg. As above-described, each of the steam generator tubes are partitioned into a plurality of segments. In this regard, the steam generator tube extending from the point 20 to the point 30 is partitioned into a plurality of segments extending, for example, from the point 20 to the point 21, from the point 21 to the point 22, and so on. Thus, the point 20 is the initial landmark and the point 30 is the final end point as above-described. Similarly, the points 21 through 29 are landmarks/end points which identify a plurality of segments extending over the length of a steam generator tube. The points 20 to 30 in Column 2 represent a single steam generator tube. It is acknowledged that in an actual steam generator and analysis thereof, the number of steam generator tubes would be greater than only one tube and therefore, multiple columns would actually be identified.

In Column 3, designations 20L through 30L are vertically spaced and positioned thereunder. Each of the designations 20L through 30L correspond to a length of a segment or the distance between consecutive endpoints designated by the points 20 to 30 in Column 2. For example, the designation 20L corresponds to a length zero because it is the starting point (i.e., point 20) or initial landmark at the end of the steam generator tube. The designation 21L is the length of the first segment or a portion of the steam generator tube extending from the (landmark) point 20 to the (end) point 21. The designation 22L is the length of the segment extending from the (landmark) point 21 to the (end) point 22, and so on.

The vertical shaded bars 40, 41 and 42 extending downwardly along the points 20 through 30, have shading that corresponds to the shading 10a, 11a and 12a, respectively, of dents 10, dings 11, and tube sheet flaws 12. Shaded bar 40 shows the segments which were analyzed for dents 10. Shaded bar 41 shows the segments that were analyzed for dings 11 and shaded bar 42 shows the segments that were analyzed for flaws 12. Visual inspection of the shaded bars 40, 41 and 42 shows that there is a gap 50, e.g., an absence of shaded bars 40, 41 and 42 between points 24 and 25. The gap 50 shows that the segment of steam generator tube length between points 24 and 25 was not analyzed for dents 10, dings 11, and tube sheet flaws 12.

FIG. 3 shows the gap analysis 2 of FIG. 2 and further includes a means to notify of or identify incomplete analysis coverage. In FIG. 3, the gap 50 (shown in FIG. 2) is identified with a shaded horizontal line 60 to notify that this portion of the steam generator tube has a gap in analysis coverage. A message box 65 is also displayed to notify of a gap in analysis coverage for a length of the modeled steam generator tube. In certain embodiments, one or both of the shaded horizontal line 60 and the message box 65 can be used.

Further, in accordance with certain embodiments of the invention, a report can be generated to list each of the segments of each of the modeled steam generator tubes, and to identify any unanalyzed areas or gaps. For example, the report would identify gap 50 shown in FIGS. 2 and 3. Based on the detection, identification and notification of gap 50, this portion (i.e., extending between the point 24 and the point 25) of the steam generator tube can be further evaluated to determine if gap 50 is acceptable or unacceptable. For example, gap 50 may be acceptable if the structure of the steam generator is such that there is an obstruction whereby it is not possible to analyze this portion (i.e., extending between the point 24 and the point 25) of the steam generator tube for dents 10, dings 11, and tube sheet flaws 12. However, if there is no obstruction or other reason as to why the segment (i.e., the length of tube extending between points 24 and 25) corresponding to gap 50 cannot be analyzed, the gap 50 may be considered unacceptable and further action can be taken to resolve the incomplete analysis coverage.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. A system for verifying complete analysis coverage in a steam generator tube inspection, in a nuclear reactor plant, the system comprising:
   a steam generator having a plurality of tubes;
   an analytical tool to generate a plant-specific map of the plurality of tubes in the steam generator, to partition each of the plurality of tubes into a plurality of segments, to measure and record a length for each of the plurality of segments, and to conduct an analysis of each of the plurality of segments to selectively analyze for one or more abnormalities;
   a computer coupled to the analytical tool to receive results of the analysis, to identify each of the plurality of segments that is inspected for the one or more abnormalities, to detect and identify each of the plurality of segments that is not inspected for the one or more abnormalities, and to generate a visual display showing the results of the analysis, wherein the visual display comprises:
      a different visual indicator representing each of the one or more abnormalities;
      a first column that identifies the plurality of segments and a character designation selected from the group consisting of numbers, letters and combinations thereof, corresponding to each of the plurality of segments; and
      one or more additional columns being horizontally spaced apart from the first column and each of the one or more additional columns corresponding to each of the one or more abnormalities for which the steam generator tube is inspected,
   wherein, when a segment of the plurality of segments is inspected for an abnormality of the one or more abnormalities, the visual indicator representing said abnormality appears in a column of the one or more additional columns corresponding to said abnormality, and said visual indicator is horizontally aligned with the character designation in the first column corresponding to said segment, and
   wherein, when a segment of the plurality of segments is not inspected for an abnormality of the one or more abnormalities, the visual indicator representing said abnormality does not appear in a portion of a column of the one or more additional columns corresponding to said abnormality that is horizontally aligned with the character designation in the first column corresponding to said segment, to identify a gap in the analysis.

2. The system of claim 1, wherein the analytical tool is selected from the group consisting of EADS and RTAA.

3. The system of claim 1, wherein the steam generator is located within a pressurized water or boiling water nuclear reactor.

4. The system of claim 1, wherein the gap in analysis coverage is visually observed as a blank space in the one or more additional columns on a computer print-out.

5. The system of claim 1, wherein the gap is visually identified by an absence of shading in the one or more additional columns and analysis coverage is identified by the presence of a shaded area in the one or more additional columns.

6. The system of claim 1, wherein the one or more abnormalities is selected from the group consisting of dents, dings, tube flaws and combinations thereof.

7. The system of claim 1, wherein the plurality of segments extend from a hot leg tube end to a cold leg tube end.

8. The system of claim 1, further comprising an assessment of a portion of the steam generator tube corresponding to the gap to determine if the gap is acceptable or unacceptable.

9. The system of claim 1, further comprising a report to identify all of the gaps identified during the steam generator tube inspection.

10. A method of method for verifying complete analysis coverage in a steam generator tube inspection of a steam generator having a plurality of tubes, in a nuclear reactor, the method comprising:
employing an analytical tool for performing steps, comprising:
generating a map of the plurality of tubes in the steam generator;
partitioning each of the plurality of tubes into a plurality of segments;
measuring and recording a length for each of the plurality of segments; and
conducting an analysis of each of the plurality of segments to selectively analyze for one or more abnormalities;
coupling a computer to the analytical tool; and
employing the computer for performing steps, comprising:
receiving results of the analysis;
analytically identifying in the results each of the plurality of segments that is analyzed for the one or more abnormalities selected and, detecting and identifying each of the plurality of segments that is not analyzed for the one or more abnormalities; and
generating a visual display, comprising:
identifying the one or more abnormalities for which the steam generator tube is inspected and a different visual indicator representing each of the one or more abnormalities;
providing a first column that identifies the plurality of segments and a character designation selected from the group consisting of numbers, letters and combinations thereof, corresponding to each of the plurality of segments; and
providing one or more additional columns horizontally spaced apart from the first column and each of the one or more additional columns corresponding to each of the one or more abnormalities for which the steam generator tube is inspected,
wherein, when a segment of the plurality of segments is inspected for an abnormality of the one or more abnormalities, the visual indicator representing said abnormality appears in a column of the one or more additional columns corresponding to said abnormality, and said visual indicator is horizontally aligned with the character designation in the first column corresponding to said segment, and
wherein, when a segment of the plurality of segments is not inspected for an abnormality of the one or more abnormalities, the visual indicator representing said abnormality does not appear in a portion of a column of the one or more additional columns corresponding to said abnormality that is horizontally aligned with the character designation in the first column corresponding to said segment, to identify a gap in the analysis.

11. The method of claim 10, wherein the gap is a blank space in the one or more additional columns on a computer print-out.

12. The method of claim 11, wherein the gap is visually identified by an absence of shading in the one or more additional columns and analysis coverage is identified by the presence of a shaded area in the one or more additional columns.

13. The method of claim 10, wherein the one or more abnormalities is selected from the group consisting of dents, dings, tube flaws and combinations thereof.

14. The method of claim 10, wherein the plurality of segments extend from a hot leg tube end to a cold leg tube end.

15. The method of claim 10, further comprising assessing the gap to determine if it is acceptable or unacceptable.

16. The method of claim 10, further comprising generating a report to identify all of the gaps identified during the steam generator tube inspection.

* * * * *